(12) United States Patent
Mandell (10) Patent No.: US 10,543,394 B2
(45) Date of Patent: Jan. 28, 2020

(54) DOUGHNUT SHAPED MULTIFUNCTION CUSHIONING DEVICE

(71) Applicant: Eleanor Leah May Mandell, Greenfield, MA (US)

(72) Inventor: Eleanor Leah May Mandell, Greenfield, MA (US)

( * ) Notice: Subject to any disclaimer, the term of this patent is extended or adjusted under 35 U.S.C. 154(b) by 575 days.

(21) Appl. No.: 14/874,490

(22) Filed: Oct. 5, 2015

(65) Prior Publication Data

US 2017/0095096 A1   Apr. 6, 2017

(51) Int. Cl.

| | |
|---|---|
| *A47G 9/10* | (2006.01) |
| *A63B 21/00* | (2006.01) |
| *A61F 5/30* | (2006.01) |
| *A47C 15/00* | (2006.01) |
| *A63B 23/035* | (2006.01) |
| *A47C 7/50* | (2006.01) |
| *A63B 21/002* | (2006.01) |
| *A63B 21/068* | (2006.01) |
| *A63B 23/04* | (2006.01) |
| *A63B 71/00* | (2006.01) |
| *A63B 71/12* | (2006.01) |

(52) U.S. Cl.
CPC ............ *A63B 21/4039* (2015.10); *A47C 7/50* (2013.01); *A47C 15/00* (2013.01); *A47G 9/10* (2013.01); *A61F 5/30* (2013.01); *A63B 21/0023* (2013.01); *A63B 21/068* (2013.01); *A63B 23/03508* (2013.01); *A47G 2009/1018* (2013.01); *A63B 21/0005* (2013.01); *A63B 23/0405* (2013.01); *A63B 2071/0063* (2013.01); *A63B 2071/125* (2013.01); *A63B 2208/0214* (2013.01); *A63B 2208/0228* (2013.01); *A63B 2208/0252* (2013.01); *A63B 2208/0276* (2013.01)

(58) Field of Classification Search
CPC ........ A41D 13/06; A41D 13/05; A41D 13/00; A41D 13/08; A47G 9/00; A47G 9/10; A47C 16/00
See application file for complete search history.

(56) References Cited

U.S. PATENT DOCUMENTS

| 967,004 | A | * | 8/1910 | Ehikian | ................ | A41D 13/065 |
| | | | | | | 2/24 |
| 2,195,817 | A | * | 4/1940 | Johnson | ............... | A41D 13/065 |
| | | | | | | 2/24 |
| 2,805,420 | A | * | 9/1957 | Spellos | .............. | A41D 13/0568 |
| | | | | | | 2/24 |
| 2,940,088 | A | * | 6/1960 | Boos | ........................ | A47G 9/10 |
| | | | | | | 5/636 |

(Continued)

FOREIGN PATENT DOCUMENTS

DE   202004013382 U1   9/2005

*Primary Examiner* — Peter M. Cuomo
*Assistant Examiner* — Ifeolu A Adeboyejo (57) ABSTRACT

A doughnut shaped multifunction cushioning device, made of foam or similar flexible resilient material, and having a doughnut hole contoured recess. During exercise, manual labor, or other human endeavor, one human body joint such as a knee or other bodily bony protuberance is placed inside the contoured recess and against the floor or other support surface. By such means the cushioning device provides one or more of the following beneficial effects: reduced risk of injury, increased comfort, body alignment, and slight traction.

10 Claims, 5 Drawing Sheets

(56) References Cited

U.S. PATENT DOCUMENTS

| | | | | |
|---|---|---|---|---|
| 3,574,397 | A | * | 4/1971 | Norriss ............ A61F 5/30 297/391 |
| 3,848,281 | A | * | 11/1974 | Mathews ............ A47G 9/10 5/490 |
| 4,567,887 | A | * | 2/1986 | Couch, Jr. ............ A61F 5/34 128/118.1 |
| 4,723,322 | A | * | 2/1988 | Shelby ............ A41D 13/065 2/16 |
| 5,471,690 | A | * | 12/1995 | McNeil ............ A47C 7/383 297/397 |
| 6,052,850 | A | * | 4/2000 | Salido ............ A47G 9/10 5/637 |
| D456,660 | S | | 5/2002 | Landvik |
| 6,536,058 | B1 | * | 3/2003 | Chang ............ A47G 9/1009 5/636 |
| D472,679 | S | | 4/2003 | Burington |
| 6,553,572 | B2 | * | 4/2003 | Fiorini ............ A41D 13/065 2/22 |
| 6,625,831 | B2 | * | 9/2003 | Laughlin ............ B29C 66/727 128/845 |
| 6,810,545 | B1 | * | 11/2004 | Darling ............ A47D 13/08 5/630 |
| 6,883,177 | B1 | * | 4/2005 | Ouellette ............ A41D 13/065 2/24 |
| 6,920,881 | B2 | * | 7/2005 | Narula ............ A61F 5/0195 128/889 |
| 7,246,391 | B2 | | 7/2007 | Brown |
| D555,251 | S | * | 11/2007 | Riach ............ D24/184 |
| D637,440 | S | * | 5/2011 | Mettler ............ D6/601 |
| D660,136 | S | | 5/2012 | Jarowenko |
| 8,220,087 | B2 | | 7/2012 | Villa et al. |
| 8,332,978 | B2 | * | 12/2012 | Warnock ............ A61F 5/05891 128/845 |
| 8,387,186 | B2 | * | 3/2013 | Yu ............ A47C 3/16 297/219.1 |
| 8,661,587 | B1 | * | 3/2014 | Leach ............ A47D 13/08 5/630 |
| D728,353 | S | * | 5/2015 | Sharratt ............ D8/374 |
| 2003/0019007 | A1 | | 1/2003 | Spencer |
| 2013/0252791 | A1 | | 9/2013 | Chang |

* cited by examiner

DOUGHNUT SHAPED MULTIFUNCTION CUSHIONING DEVICE

CROSS-REFERENCE TO RELATED APPLICATIONS

Not Applicable

The following is a tabulation of some prior art that presently appears relevant.

U.S. Patents

| Patent Number | Kind Code | Issue Date | Patentee |
|---|---|---|---|
| 8,220,087 | B2 | Jul. 17, 2012 | Villa, Giovanni et al |
| 7,246,391 | B2 | Jul. 24, 2007 | Brown, Leslie M. |
| 6,883,177 | B1 | Apr. 26, 2005 | Oullette, Daniel et al |
| 4,723,322 | A | Feb. 9, 1988 | Shelby, James E. |
| 2,195,817 | A | Apr. 2, 1940 | Jacob, Johnson |
| D660136 | S | May 22, 2012 | Jarowenko, Anita L. |
| D472679 | S | Apr. 1, 2003 | Burington, Wayne L. |
| D456660 | S | May 7, 2002 | Landvik, Dag |

U.S. Patent Application Publications

| Publication Nr. | Kind Code | Pub. Date | Applicant |
|---|---|---|---|
| 20130252791 | A1 | Sep. 26, 2013 | Chang, Kenneth |
| 20030019007 | A1 | Jan. 30, 2003 | Spencer, Harvey Lee |

Foreign Patent Documents

| Foreign Doc. Nr. | Cty. Code | Kind Code | Pub. Dt. | App. or Patentee |
|---|---|---|---|---|
| 202004013382 | DE | U1 | Sep. 29, 2005 | Schenkhut, Fraatz Ingrid et al |

BACKGROUND—PRIOR ART

Because of the multifunction nature of the present device, prior art is in more than one field of invention. It is in knee pads for kneeling labor, yoga props and padding, meditation supports, and miscellaneous other cushions for the head and body.

1. Prior Art—Kneepads for Kneeling Manual Labor

The knee is susceptible to injury and gradual deterioration, especially with overuse and age. To address the need for knee protection during kneeling manual labor, many kneepads have a horseshoe shape so that the top of the knee fits inside the upper curve of the horseshoe, and the shin passes through the horseshoe opening. Others have shaping or molding that requires a specific orientation. Existing kneepads are not easily adapted for different sizes of knee or leg and are relatively complex and therefore expensive to produce. They are often bulky, have straps, or they have shaping that makes them hard to grasp quickly. For quicker tasks or shorter time spent on the knee, they are often considered too much trouble to locate, orient properly, strap on, and so forth. So the laborer will go without a kneepad and suffer incremental gradual damage to the knee.

U.S. Pat. No. 4,723,322, Feb. 9, 1988, inventor James E. Shelby, claims a strapless molded knee-pad with a contoured indent. The combination of the large bottom surface and no through-hole, means that the device is hard to grasp quickly. The large bottom surface makes the device bulky and somewhat inconvenient to store, retrieve, and use. What is needed is an improvement to the U.S. Pat. No. 4,723,322 design wherein the kneepad is convenient to grasp and reposition, and is less bulky.

U.S. D660136, May 22, 2012, Anita L. Jarowenko, has a similar large bottom surface, and no through-hole.

There are larger one-piece knee cushion supports designed to protect both knees at once, which have recesses or contoured indents to hold the knees. These are bulky and not adaptable for different knee spacing or positioning. An example is shown in U.S. D472679, Apr. 1, 2003, inventor Wayne L. Burington. There is a need for a lightweight, and versatile kneepad that fits easily in a pants pocket, straps quickly to a tool caddy, and is not cumbersome.

Patent DE 202004013382, Nov. 3, 2005, inventor Fraatz Ingrid Schenkhut, claims a circular knee cushion that is lightweight and inexpensive. This knee cushion is ring shaped rather than horseshoe shaped, so in its strapless form it has the advantages of not needing the finicky attention of a particular orientation during use. In the DE 202004013382 knee cushion, there is a flat upper surface, a flat lower surface, and a columnar recess from top to bottom in the middle of the cushion. The knee to be cushioned goes into the recess, with the cushion between the knee and the floor. The sides of the recess meet the top surface with an abrupt edge, like a corner, so that a cross section of the ring shaped body forms a rectangle with 90 degree corners. This design has the disadvantage of no shaping to cup the knee inside the recess. The shape of the recess is not ergonomic and not contoured to support the rounded shape of the human knee during kneeling manual labor. Also the columnar recess with abrupt edges is less able to accommodate knees of different sizes or shapes. What is needed is an improvement to the DE 202004013382 design wherein the recess is contoured, distributing the body weight against a larger surface area and thereby increasing the comfort of the knee as it presses against the cushion body. An additional desired improvement would be to allow, from one configuration, for knees of many different sizes and shapes to rest within, protected from the floor or other supporting surface.

2. Prior Art—Yoga Props and Padding, and Meditation Supports

Yoga continues to gain popularity around the world as a boon to mankind. Many yoga styles have been developed to allow people of different ages, fitness levels, injury status, and body types to reap the considerable benefits to mind and body from this ancient art. A session executing yoga is called a yoga practice. Also a regular routine of yoga is called a yoga practice. People who execute yoga are called yoga practitioners. The positions used during yoga to realize its benefits, are called poses, postures, or asanas.

In yoga, many props, padding devices, and cushioning approaches are used for specific purposes, and some, like the standard yoga block or standard yoga blanket, have the advantage of being multifunction. But current yoga prop choices have deficiencies, and considering the vast population of yoga practitioners and the benefits to humankind that yoga can provide, there is a need for a simple, lightweight, inexpensive multifunction device that provides cushioning, support, and alignment, and that is adaptable to all styles of yoga and also the sizes, shapes, and abilities of people practicing yoga. Beginning yoga practitioners would especially benefit from increased comfort and reduced risk of injury, to encourage them to maintain their practice.

In yoga classes today, knee cushioning in poses where the knee bears weight, such as hands and knees pose, or lunge pose, is ad hoc. Practitioners fold over their mats to provide more layers between their knee and the floor, or they place a folded yoga blanket under their knees, or they grab their socks and bunch them up under their knees. This finicky positioning of cumbersome articles that are not purposed designed, is a lot of trouble, and so people frequently expose themselves to potential knee damage by not using knee protection.

Many yoga practitioners struggle with strain or injury in their wrists. Downward facing dog pose is used frequently during yoga classes for its many benefits, but this pose places great body weight on the wrists. There is a need for a simple, inexpensive prop that can be placed quickly under the palm of the hand during poses that require the wrist to bear weight. When the palm is lifted a little bit, the wrist is not so sharply bent and weight is redistributed away from the wrist itself and down into the palm and the rest of the hand, reducing strain and the risk of injury. U.S. Pat. No. 8,460,160, inventor Elizabeth M. Andrews, issue date Jun. 11, 2013 is for a wrist saving yoga device consisting of a rectangular cushioned pad to be strapped to the palm, lifting it slightly and thereby achieving the desired relief from the sharp wrist bend and thereby also achieving weight redistribution. But the weight bearing surface of the U.S. Pat. No. 8,460,160 wrist saver device, though cushioned, is not contoured to fit the bones of the palm and therefore does not provide the additional degree of comfort that contouring would provide. Also the device has the disadvantage of being single-purpose and the required strap makes it relatively complex in design.

In yoga seated poses such as hero pose or staff pose, the ideal is to achieve an erect spinal alignment without undue strain. This is easier if each sitbone, namely the bone inside each buttock that bears weight during sitting, is lifted. The degree of lift required varies by person, from a couple of centimeters, to much more. Most frequently practitioners use a standard yoga block or a folded blanket in seated poses, to raise the sitbones and achieve proper spinal alignment with ease. A standard yoga block is a few inches high at the lowest setting, which often provides more height than is needed. It is relatively hard, doesn't contour to the sitbones, and is bulky. A folded blanket allows for greater flexibility in degree of lift and is soft, but it needs to be folded correctly to provide the desired lift and it is finicky to position correctly. Also, there is always the suspicion that shared blankets in a public yoga class might not be laundered frequently, or might accumulate undesired fragrances from body products such as shampoo or perfume. There are single purpose meditation cushions that are specifically designed to provide comfort and lift during sitting, but these are bulky and not commonly used during yoga.

At the end of most yoga practices is the restorative pose called corpse pose, which is a deep rest while lying on the back. Sometimes a folded blanket is used to raise the head in such a way that the chin points slightly downward, thereby achieving a particular neck alignment which is known to be calming to the nervous system. But a deeper relaxation could be achieved if the head were not only slightly lifted with the chin angled downward, but also prevented from rolling side to side in cases where either the head and neck achieved a further degree of muscular relaxation, or the practitioner actually fell asleep. In corpse pose with no blanket under the head, or in corpse pose with a blanket under the head, the practitioner is prevented from achieving a further level of relaxation by the possibility that the head could roll to one side or the other. What is needed is a device that lifts the head a little bit and brings the chin downward, thereby calming the nervous system, and also provides side to side support, preventing the head from rolling to one side or the other.

3. Prior Art—Other Doughnut Shaped Cushions for the Head and Body

Doughnut shaped cushions exist in the form of coccyx pillows, designed to relieve pressure on the base of the spine, or provide comfort to hemorroid sufferers or others with injury or disease in that area. The two sitbones rest directly on either side of a large circular cushion body. These cushions serve a specific single-use medical purpose, which is to remove all weight while sitting, from the base of the spine. They contain no contouring to cup the sitbones themselves.

Doughnut shaped cushions also exist to cushion an infant's head. These single-purpose cushions are not of sufficient density or appropriate design to cushion adult human bones during weight-bearing activity.

U.S. D456660, Aug. 7, 1990, inventor Dag Landvik, shows a small round contoured head-pillow that has a contoured top surface as well as a contoured bottom surface. This pillow lacks a through-hole, that would make it easier to grasp, reposition, or compress for storage.

SUMMARY

This multipurpose doughnut shaped cushioning device is designed to cup within its contoured recess one human skeletal joint, such as a knee or elbow, or one bony protuberance, such as the back of the head. By such cupping or enclosing, it cushions the joint or protuberance from the floor or supporting surface, or provides traction, alignment, or lift while seating.

Advantages

The advantages of this doughnut shaped multifunction cushioning device, are discussed below.

1. Advantages as a Kneepad

The present device can be used as a kneepad during kneeling manual labor. By virtue of its circular shape in most embodiments, it requires no specific orientation during use, so is less cumbersome than traditional horseshoe or elaborately molded kneepads that require a specific orientation. The simple one-piece lightweight doughnut shaped design allows for inexpensive production, packaging, and shipping. Relative to one-piece knee cushions with indents or recesses to support both knees at once, the present design is more versatile as, using one device for each knee, it allows for a variety of different knee positions, and is less bulky. The recess makes it easy to compress and stick in a pants pocket, and if the laborer's tool caddy has a strap, the present device can be strung on the strap like a roll of tape for quick retrieval.

Compared to the device of U.S. Pat. No. 4,723,322, the present design by virtue of the doughnut hole recess and the contours of the bottom shoulders, is easier to grasp and reposition. Also the smaller bottom surface makes it less bulky.

Compared to the circular knee cushion of patent DE 202004013382, the present design has the advantage of a curved contoured recess. This contoured recess cups the knee ergonomically and distributes the body weight against a larger cushion surface area, increasing comfort. There is no abrupt top recess corner to irritate the flesh. Also the gradual contour of the top inner shoulder of the present design, is able to accommodate many different shapes and sizes of knee. The doughnut shape is largely formed by the four shoulders, and the combination of the four contoured shoulders create an ergonomic shape that is very easy to grasp. Therefore the present design represents an important improvement over the circular knee cushion of DE 202004013382.

2. Advantages in Yoga

In yoga kneeling poses when used to cushion the knee, the current design in a medium size allows for speedy placement as the knee slips quickly into the contoured recess. People of different sizes and shapes can use the same medium size of device since the contoured recess accommodates different sizes and shapes of knee. The weight of the body passes through the knee, which is suspended above the floor in a comfortable, flexible, resilient cushion. When it is time to move to the next yoga pose during the yoga session, the device is ergonomic to grasp by virtue of its curves, and it can quickly be placed to the side until it is needed again. For kneeling poses during yoga, the present invention provides a better solution than the current approaches of folding up the yoga mat, sliding a yoga blanket under the knees, or bunching up socks and putting them under the knees.

In a smaller size, the current design protects the wrists during yoga poses where weight is borne by the wrists. The bone of the palm is placed in the cushion recess and the contours of the recess echo the physiology of the wrist and palm. The device lifts the palm, thereby providing relief from a sharp wrist angle that can cause strain and injury. At the same time the weight of the body is channeled down into the palm and the rest of the hand, rather than landing on the wrist. Because the device has no strap and is multifunction, it is more likely to be used in a yoga practice as a wrist cushion device than a single purpose device. Also the contoured recess is more ergonomic and more comfortable than the rectangular cushion pad of the wrist saving device claimed by U.S. Pat. No. 8,460,160.

A matching pair of the present multifunction cushioning devices in a medium size can be placed one under each sitbone during yoga seated poses, thereby providing a small amount of lift and facilitating proper erect spinal alignment without strain. Each sitbone would nestle cupped within one cushion device, inside the contoured recess. They could be stacked if more lift is needed. The devices can be moved further apart or closer together depending on the distance between the sitbones of that individual. If a great deal of lift is needed, the devices can be placed on top of a standard yoga block, thereby achieving the desired height and stability of the block, as well as the contoured comfort of the current device.

Yoga corpse pose is a deep rest while lying on the back, at the end of a yoga practice. This period of rest allows the body to fully absorb the benefits of the practice. In corpse pose, the present device in a larger size and with a recess of larger diameter, can be placed under the back of the head. This aligns the neck so that the chin points downward thereby achieving the desired enhanced calming effect upon the nervous system. At the same time the cushion body gently but securely cups the head and prevents it from falling to one side or the other, thereby allowing deeper relaxation by the yoga practitioner. The enhanced safety will be both physical and psychological as the practitioner perceives through the supporting pressure and the comfort of the contoured recess, that he or she is supported and safe in the posture. These are the advantages over the current custom of using a folded blanket to lift the head during corpse pose.

DRAWINGS—REFERENCE NUMERALS

1 contoured recess
2 top inner shoulder
3 top outer shoulder
4 bottom inner shoulder
5 bottom outer shoulder
6 top surface
7 bottom surface
8 channel or groove in the top

DETAILED DESCRIPTION

Figure 1:
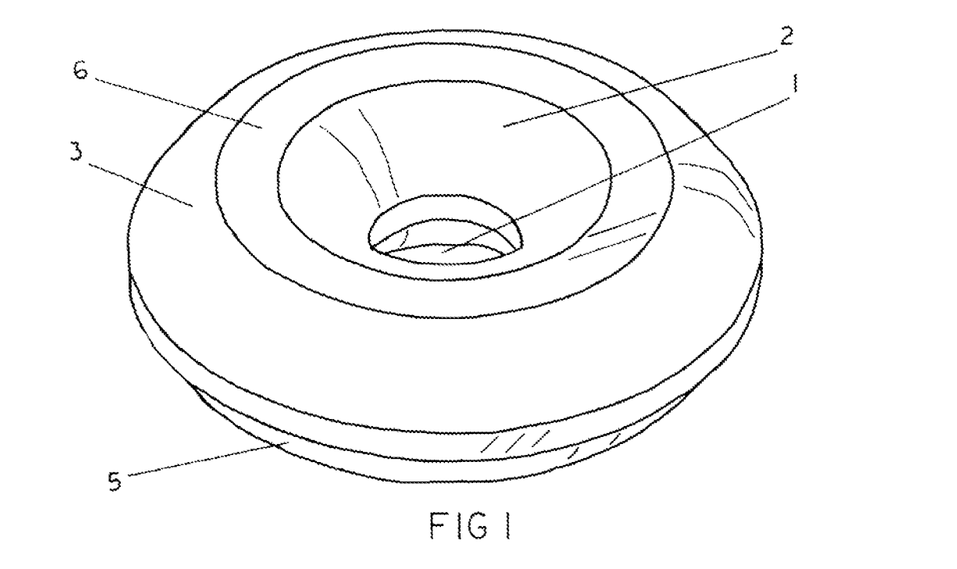
FIG. 1 shows a perspective view of the device in a first embodiment
Figure 2:
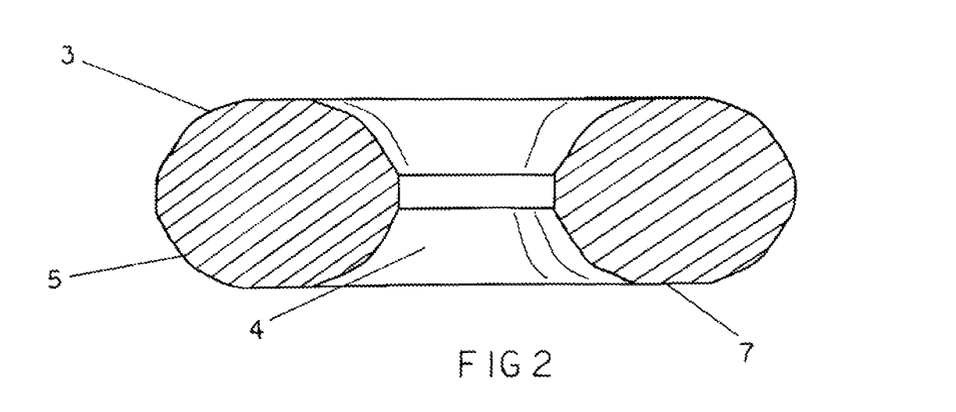
FIG. 2 shows a cross-section view of the device in the first embodiment

FIGS. 1-2 illustrate different views of one embodiment of the doughnut shaped multifunction cushioning device. The device has a circular doughnut shaped body. The body is made of foam or similar flexible resilient material, of sufficient density to support the weight of an adult human. The body has a hole, void, or recess 1 from top to bottom. The functional effect of this recess is predominantly achieved by the acclivity or slope of the top inner shoulder 2 which shapes the top of the recess. The recess is meant to contain within it, one human body joint such as a knee, or one human bony protuberance such as the back of the head, against a floor or other supporting surface. A cushioning effect is achieved by the distribution of body weight over the flexible resilient surface of the top inner shoulder 2. The device has a bottom inner shoulder 4 that forms the bottom of the recess 1. The slope of the top inner shoulder in conjunction with the slope of the bottom inner shoulder, together achieve a gradual diminution of resilient foam material towards the center of the recess. A second cushioning effect is achieved by the compression of the resilient foam body material inside the recess, and is enhanced by this gradual diminution of material towards the center. The device has a top outer shoulder 3 that defines the circular top outer edge of the body, and a bottom outer shoulder 5 that forms the circular bottom outer edge of the body. The device has a flat top surface 6 and a flat bottom surface 7.

The approximate proportions of the embodiment shown in FIGS. 1-2 would be useful as a knee pad and in many yoga postures. This is because the combination of the predetermined circumference of the contoured recess, and the acclivity of the top inner shoulder, are able to provide support and cushioning for knees and other body joints of many sizes. Also the flexible resilient material from which the device is made, is of sufficient density to support the weight of an adult human.

The relative proportions of the device components, such as the diameter of the recess relative to the rest of the body, the width of the top surface or the bottom surface, or the specific acclivities of the four shoulders, can be varied to best suit a specific purpose for which the device is intended. Alternatively they can be varied to achieve the most universal multifunction qualities.

Figure 3:
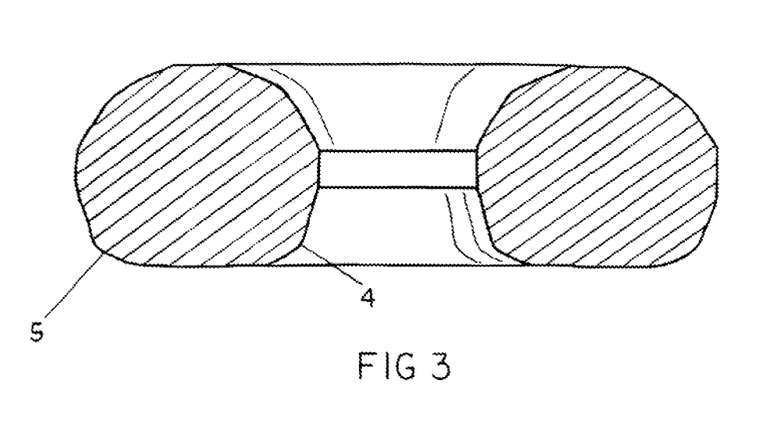
FIG. 3 shows a cross-section view of the device in a second embodiment

FIG. 3 illustrates an alternative embodiment in which the acclivities of the bottom inner shoulder 4 and the bottom outer shoulder 5 are modified to provide a larger base. This modification would be useful when additional cushioning and stability are desired, for example to cushion the top of the head in yoga headstand.

Figure 4:
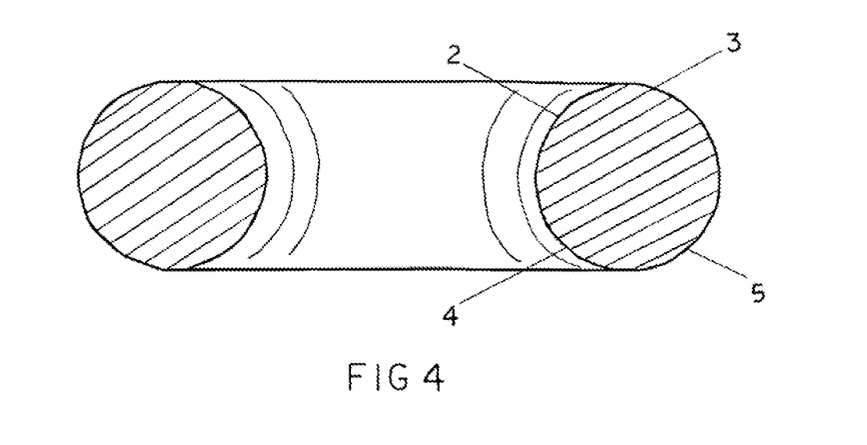
FIG. 4 shows a cross-section view of the device in a third embodiment

FIG. 4 illustrates an alternative embodiment in which the top surface and bottom surface are reduced to zero width, and the four shoulders form a circle, so that the device is a torus shape. Also, in this particular torus shape, the recess diameter is larger relative to the body.

Figure 5:
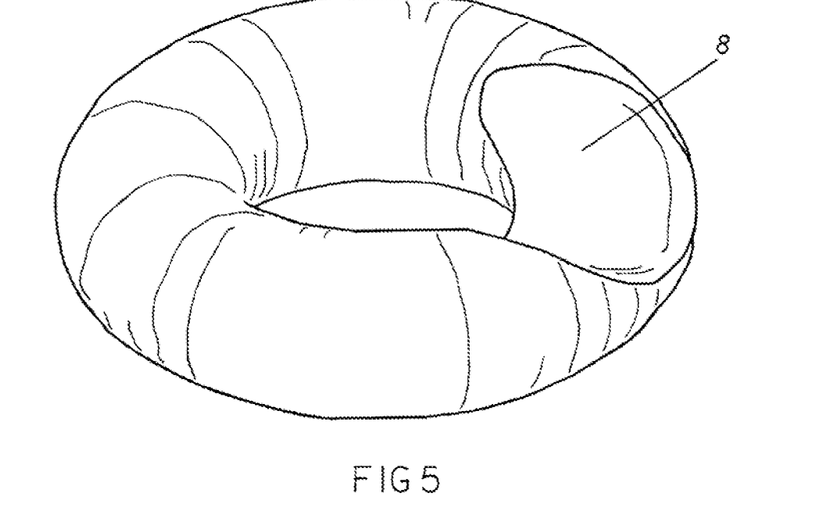
FIG. 5 shows a perspective view of the device in a fourth embodiment in which there is a shaped groove in the top of the device

FIG. 5 illustrates a perspective view of an alternative embodiment of the present device wherein the doughnut shaped body is not even in size and proportion all the way around the cushion body. Instead it contains predetermined additional shaping such as a bulge on one side, or a cut-out portion of the top surface 8. Such modifications would allow for increased comfort and/or support during a specific use. An example would be to provide a groove in the top surface to accommodate the neck during use as head support during yoga corpse pose.

Figure 6:
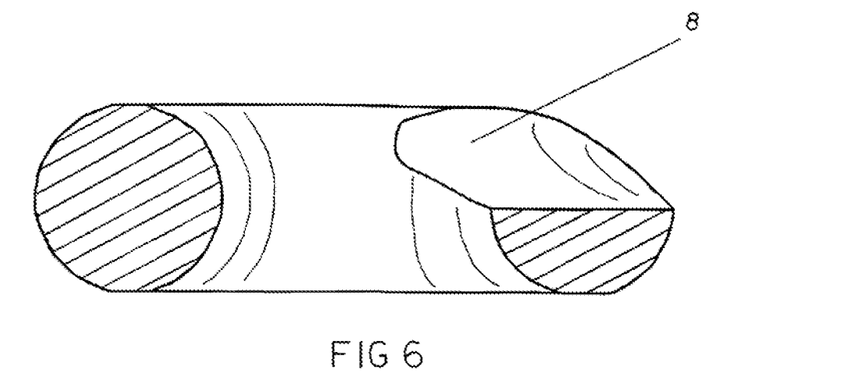
FIG. 6 shows a cross-section view of the device in the fourth embodiment

FIG. 6 illustrates a cross-section view of the alternative embodiment of FIG. 5.

Figure 7:
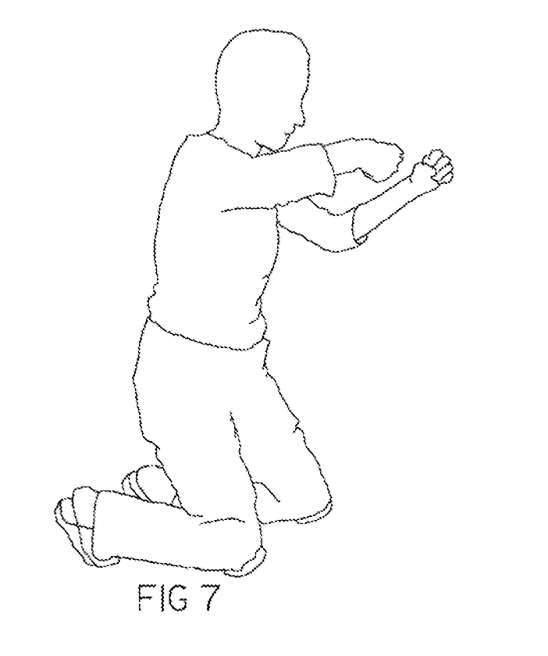
FIG. 7 shows the device in use as a kneepad in kneeling manual labor

FIG. 7 illustrates the device used as a kneepad for kneeling manual labor. The knee fits into the contoured recess, thereby increasing comfort and reducing risk of injury. The small size of the device and its flexible nature, make it easy to stick into the pants pocket or tool caddy of a working person. Or for general home tasks, it can be put on a hook in a closet and quickly retrieved when cushioning is needed for the knee.

Figure 8:
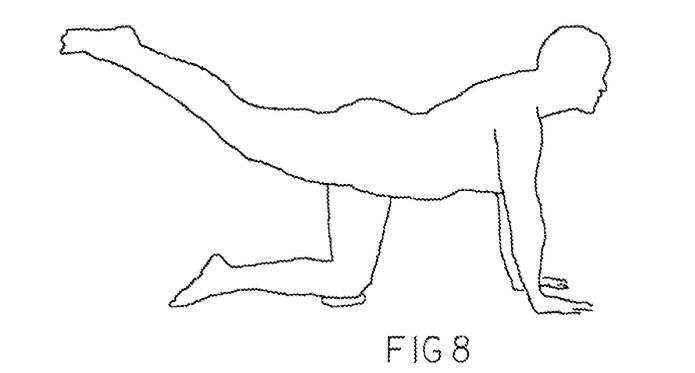
FIG. 8 shows the device in use in yoga hands and knees pose

FIG. 8 illustrates the device in a variation of yoga hands and knees pose, underneath the knees. The contoured recess cups and supports the knee.

Figure 9:
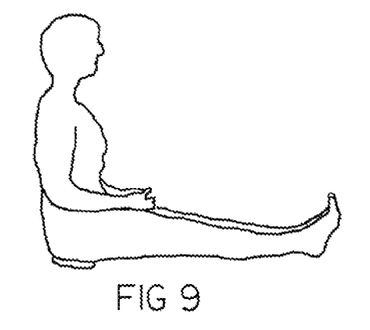
FIG. 9 shows the device in use in yoga hero sitting pose

FIG. 9 illustrates the device in yoga seated staff pose, one under each sitbone. In this way the sitbones are cushioned and also the slight lift allows for an erect spine without strain. If more lift is desired, the devices can be stacked with two under each sitbone. In this use the contours of the top outer shoulder of the device provide additional comfort since the flesh of the buttocks rests on the top outer shoulder as well as the top inner shoulder of the device.

Figure 10:
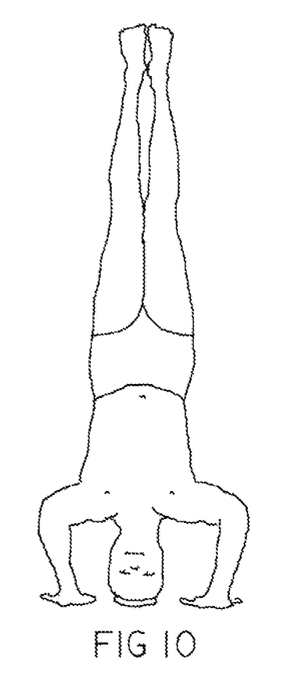
FIG. 10 shows the device in use in yoga headstand pose

FIG. 10 illustrates the device in yoga headstand. Headstand is considered a more advanced pose, and can put strain on the neck. In this use the curve of the top of the head is cushioned by the contoured recess. The additional cushion bulk and stability of the embodiment in FIG. 3, where the bottom of the cushion body is thicker than in FIGS. 1-2, reduce risk of injury to the neck.

Figure 11:
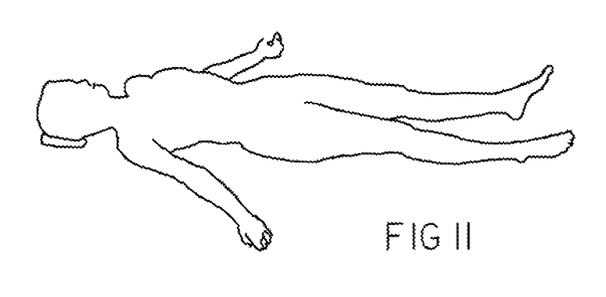
FIG. 11 shows the device in use in yoga corpse pose

FIG. 11 illustrates the device in yoga corpse pose, under the back of the head. Corpse pose is a deep rest while lying on the back, that allows the practitioner to fully absorb all of the benefits of their practice. The embodiment shown in FIG. 4, in which the recess has a larger diameter relative to the rest of the cushion body, supports the broader curves of the back of the head. The slight lift of the head allows the chin to point downwards, achieving the desired enhanced calming effect to the nervous system. Also, the head is prevented by the doughnut shape, from rolling to one side or the other. The physical and psychological security offered by the use of the device during corpse pose, will allow the practitioner to achieve a deeper relaxation and thereby perhaps enhanced benefits from the entire practice.

CONCLUSION, RAMIFICATIONS, AND SCOPE

There is a need for a lightweight, inexpensive, strapless effective kneepad that is convenient to use and store, and that accommodates knees of different sizes and people of different body weights. The current device satisfies this need. The contoured recess provides versatility, comfort, and ease of use for kneeling manual labor.

The best yoga props are simple and multifunction, and help people of all abilities maintain their yoga practice by increasing comfort, reducing risk of injury, and allowing greater ease in the postures. One purpose of the current device is to facilitate a safe and healthful yoga practice through the uses described above, for everyone who embraces yoga to enhance their lives.

In addition to the uses of the present device to support commonly executed poses or groups of poses, discussed above, there are more yoga-related ramifications. During forearm balances it can cushion the bones of the elbow. During seated right-angle pose, it can cup the heel and prevent the leg from rolling outwards or inwards. Preventing such rotation is otherwise a considerable strain in this pose. During poses where weight is borne by the shin and top of the foot, such as hero pose or camel pose, the current device can be placed underneath the top of the foot and compensate for the practitioner's inability to point the foot completely. During forward bends it can be placed on top of a block and used as a rest for the top of the head. In poses where the practitioner is lying on the front of the body, it can cushion the hipbones from the floor. Also in these poses it can be placed under the forehead, lifting the nose from the floor and aligning the neck. This will allow the head to rest on the floor looking straight down, without turning from one side to the other, thereby creating ease in the neck and shoulders.

The yoga community is likely to embrace the potential of this device and find other ways to use it, not described here. For example, one yoga teacher who was consulted for this patent, immediately saw a benefit as an alignment and support device for people with scoliosis who did yoga for scoliosis therapy.

The device will find its way into related therapeutic fields. Very likely it will be used to provide alignment during massage or acupuncture treatments, or traction or support during physical therapy. It could be used as a coccyx pillow for some people.

A matching pair of them could be used as a small portable cushion against hard stadium seats, church pews, or other non-ergonomic seating. It could be placed against the side of the head for napping in the car or on public transport, or on an airplane. It could be used in other exercise fields, such as to cushion runners during warm-up stretches.

The present device possesses versatility and universal utility, with potential to benefit people in many different endeavors. It is lightweight, inexpensive to produce, easy to pack and ship, non-breakable, ergonomic, and highly useful. The contoured recess provides support over a large surface area. The doughnut shape and connotation make it appealing and attractive, and the hole makes it easy to grasp and place during use.

This device by its simplicity, lends itself to modification of the relative proportions of the components. But without knowledge gained from extensive usage over a period of time by different people, it is difficult to predict which precise shape and proportion will ultimately be the preferred embodiment. There are likely to be variations on the doughnut shape, that will evolve for specific uses, for which the specifics cannot be predicted now, but which will still fall within the scope of this invention. As the device is used in the future by people of different sizes and for different purposes, more will become known about the best configurations or embodiments, for different situations. The above embodiment descriptions represent the best guess of the inventor at this time, of the suitability of slightly different shapes of the device, for different purposes. These embodiment descriptions are not meant to limit the device to these specific embodiments, but instead to provide a few variations that demonstrate different utility and thereby to suggest that in the future there will be other useful variations. The overall size of the device in different embodiments will of course also contribute to different utility.

Although the description above contains many specificities, these should not be construed as limiting the scope of the invention but as merely providing illustrations of some of the presently preferred embodiments of this invention. The scope of the invention should be determined by the appended claims and their legal equivalents, rather than by the examples given.

What is claimed is:

1. A cushion that supports a body joint of a user above a support surface, the cushion comprising
    a doughnut shaped body having an outer diameter of from approximately 6 cm to approximately 15 cm and having height of from approximately 2 cm to approximately 6 cm,
    said body formed of foam or similar flexible resilient material, said material of sufficient density to cushion the weight of an adult human,
    said body including a doughnut hole shaped cushion recess through said body from top to bottom,
    a top outer shoulder forming the top outside edge of said body and having a convex shape of predetermined acclivity,
    a bottom outer shoulder forming the bottom outside edge of said body and having a convex shape of predetermined acclivity,
    a top inner shoulder forming the top of said cushion recess and having a convex shape of predetermined acclivity,
    a bottom inner shoulder forming the bottom of said cushion recess and having a convex shape of predetermined acclivity,
    a top surface,
    a bottom surface,
    whereby during exercise, manual labor, therapeutic procedure or other human endeavor, said body joint is placed inside said cushion recess thereby reducing risk of injury, increasing comfort, or providing alignment or beneficial traction.

2. The cushion of claim 1 wherein either said top surface or said bottom surface includes protrusions, texturing, or sticky surfacing thereby inhibiting sliding and increasing stability.

3. The cushion of claim 1 wherein said top surface and said bottom surface include protrusions, texturing, or sticky surfacing thereby inhibiting sliding and increasing stability.

4. The cushion of claim 1 wherein any of the said four shoulders, namely said top inner shoulder, said top outer shoulder, said bottom inner shoulder, and said bottom outer shoulder, have the same acclivities or have different acclivities.

5. The cushion of claim 1 wherein said top surface is reduced to zero width so that said top inner shoulder joins directly with said top outer shoulder.

6. The cushion of claim 1 wherein said bottom surface is reduced to zero width so that said bottom inner shoulder joins directly with said bottom outer shoulder.

7. The cushion of claim 1 wherein said top surface and said bottom surface are reduced to zero width, and said top inner shoulder, said top outer shoulder, said bottom inner shoulder, and said bottom outer shoulder, form by their acclivities a circle, thereby making said cushion into a torus shape.

8. The cushion of claim 1 wherein said top surface and said bottom surface have interconnecting protrusions thereby increasing stability if a plurality of said cushions are stacked.

9. The cushion of claim 1 wherein said doughnut shape is the same size and shape around its circumference such that a cross sections of said body at any point, form the identical geometric shape.

10. The cushion of claim 1 wherein said top surface has a groove, indent, or other shaping, thereby facilitating a specific use or orientation.

* * * * *